United States Patent [19]

Anderson et al.

[11] 4,406,690
[45] Sep. 27, 1983

[54] CERTAIN ARALKYLOXY OR ARALKYLTHIO-PYRIDYL-PHTHALIMIDES AND THEIR USE AS HERBICIDES

[75] Inventors: Richard J. Anderson, Palo Alto; Michael M. Leippe, Boulder Creek, both of Calif.

[73] Assignee: Zoecon Corporation, Palo Alto, Calif.

[21] Appl. No.: 348,555

[22] Filed: Feb. 12, 1982

Related U.S. Application Data

[63] Continuation-in-part of Ser. No. 273,834, Jun. 15, 1981, abandoned.

[51] Int. Cl.³ .................... A01N 43/40; C07D 401/04
[52] U.S. Cl. ......................................... 71/94; 546/273
[58] Field of Search ............................ 546/273; 71/94

[56] References Cited

U.S. PATENT DOCUMENTS 4,001,272  1/1977  Goddard ............................ 260/326
4,124,375  11/1978  Bollinger et al. ...................... 71/96

OTHER PUBLICATIONS

CA 94:15589d (1981)—Yoshida et al.

*Primary Examiner*—Alan L. Rotman
*Attorney, Agent, or Firm*—Jacqueline S. Larson; Donald W. Erickson

[57] ABSTRACT

N-substituted pyridyl tetrahydrophthalimides, intermediates therefor and synthesis thereof which are useful herbicides.

27 Claims, No Drawings

CERTAIN ARALKYLOXY OR ARALKYLTHIO-PYRIDYL-PHTHALIMIDES AND THEIR USE AS HERBICIDES

This is a continuation-in-part of Ser. No. 273,834, filed on June 15, 1981, abandoned the entire disclosure of which is incorporated herein by reference.

This invention relates to N-substituted pyridyl tetrahydrophthalimides, intermediates therefor and synthesis thereof which are useful herbicides.

The N-substituted pyridyl tetrahydrophthalimides of the present invention are represented by the following formula (A):

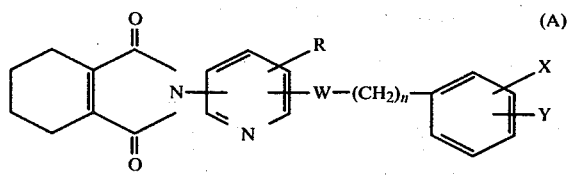

wherein,
n is one, two or three;
R is hydrogen, bromo, chloro, fluoro or iodo;
W is oxygen or sulfur; and
each of X and Y is, independently, selected from hydrogen, bromo, chloro, fluoro, iodo, lower alkyl, lower alkoxy, lower thioalkyl, lower haloalkyl, lower haloalkoxy, nitro, lower alkoxycarbonyl and cyano.

Hereinafter, each of n, R, W, X and Y is as defined above, unless otherwise specified.

The compounds of formula A are prepared by the reaction of 3,4,5,6-tetrahydrophthalic anhydride with a substituted amino-pyridine of formula (I).

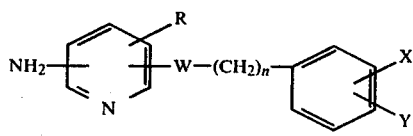

The reaction is conducted at a temperature above room temperature such as the reflux temperature of the reaction mixture and is generally complete within a few hours or less.

The substituted amino-pyridine compounds of formula (I) wherein W is oxygen can be prepared by the reaction of a hydroxy-nitropyridine with a substituted phenalkyl halide to obtain the corresponding substituted nitro-pyridine which is reduced to the desired substituted amino-pyridine of formula (I). For example, the reaction of 5-hydroxy-2-nitropyridine and 4-chlorobenzyl bromide gives 5-(4-chlorobenzyloxy)-2-nitropyridine which is then reduced to 2-amino-5-(4-chlorobenzyloxy)-pyridine of formula I. Alternatively, the compounds of formula I can be prepared by the reaction of a halo-nitropyridine with a substituted phenalkyl alcohol or substituted phenalkyl thiol followed by reduction of the nitro group. For example, the reaction of 2-chloro-5-nitropyridine and 4-bromobenzyl alcohol gives 2-(4-bromobenzyloxy)-5-nitropyridine which is then reduced using, for example, iron powder to give 5-amino-2-(4-bromobenzyloxy)pyridine of formula (I).

The term "lower alkyl," as used herein, refers to an alkyl group of one to six carbon atoms.

The term "lower alkoxy," as used herein, refers to an alkoxy group of one to six carbon atoms.

The term "lower alkoxycarbonyl," as used herein, refers to an alkoxycarbonyl group of two to six carbon atoms.

The term "lower thioalkyl," as used herein, refers to a thioalkyl group of one of six carbon atoms such as methylthio.

The term "lower haloalkyl," as used herein, refers to a haloalkyl group of one to six carbon atoms substituted with at least one halo atom such as trifluoromethyl, difluoromethyl, trichloromethyl, dichloromethyl, fluoromethyl or chloromethyl.

The term "lower haloalkoxy," as used herein, refers to a haloalkoxy group of one to six carbon atoms substituted with at least one halo atom such as difluoromethoxy, dichlormethoxy, trifluoromethoxy, trichloromethoxy, fluoromethoxy or chloromethoxy.

The compounds of formula (A) are useful for the control of weeds using pre- and/or post-emergent treatments. The compounds can be applied in the form of dusts, granules, solutions, emulsions, wettable powders and suspensions. Application of a compound of the present invention is made according to conventional procedure using from about one-fourth to ten pounds per acre. Methods of preparing herbicidal formulations which can be used with a compound of the present invention are described in the literature along with suitable liquid and solid carriers such as in U.S. Pat. Nos. 4,192,669, 4,163,661 and 4,072,499 which are incorporated herein by reference. The compounds of the present invention have activity on broadleaf plants and grassy plants. The optimum usage of a compound of the present invention is readily determinable by one of ordinary skill in the art using routine testing such as greenhouse testing and small plot testing.

In another embodiment of the present invention, there are provided compounds of formula (B) and (C) which have useful herbicidal activity.

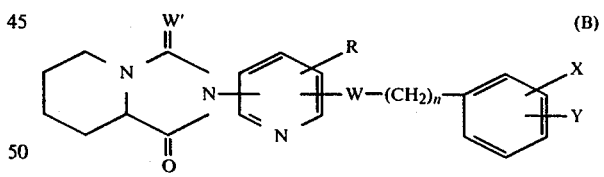

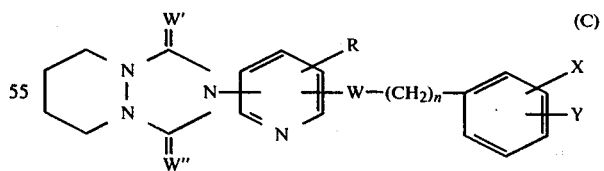

In the above formulas, each of W' and W" is oxygen or sulfur and each of R, n, W, X and Y is as defined hereinabove.

The following examples are provided to illustrate the practice of the present invention. Temperature is given in degrees centigrade. All parts are by weight unless otherwise indicated. RT means room temperature. DMSO refers to dimethylsulfoxide. DMF refers to dimethylformamide.

EXAMPLE 1

To a stirred mixture of NaH (0.77 g) and DMSO is slowly added 4-chlorophenethyl alcohol (5 g) in DMSO (20 ml) while maintaining the temperature at or below 32°. After gas evolution stops, 2-chloro-5-nitropyridine (4 g) is added in small portions while maintaining temperature below 25°. After stirring about 1 hour, the reaction is poured onto about 300 g ice and then filtered. The solid is dissolved in ether, washed with water, dried (sodium sulfate) and solvent evaporated to give 2-(4-chlorophenethoxy)-5-nitropyridine, a grey solid.

A mixture of 2-(4-chlorophenethoxy)-5-nitropyridine (1 g), ammonium chloride (1.9 g), ethanol (40 ml) and water (20 ml) is heated to 70° and then iron powder (1 g), under nitrogen, is added in small portions over about 15 minutes. Heating is continued about 2 hours after the addition of iron is complete. The reaction is cooled and stripped. The residue is taken up in ether, washed with water, dried and solvent evaporated to give 5-amino-2-(4-chlorophenethoxy)pyridine.

A mixture of 3,4,5,6-tetrahydrophthalic anhydride (0.4 g), 5-amino-2-(4-chlorophenethoxy)pyridine (0.6 g) and acetic acid (20 ml) is heated to reflux. After about 1.5 hours, the reaction is cooled and concentrated to about one-half volume. On standing a crystalline solid precipitation which is collected by filtration and washed with 10% ethyl acetate/hexane to yield N-[2-(4-chlorophenethoxy)-5-pyridyl]-3,4,5,6-tetrahydrophthalimide.

NMR (CDCl$_3$) δ1.80 (br m, 4, ring CH$_2$) 2.39 (br m, 4, allylic ring CH$_2$) 3.03 (t, 2 φ CH$_2$) 4.5 (t, 2, OCH$_2$) 6.65–8.15 (m, 3, pyridyl H) and 7.14 ppm (S, 4, φ H).

EXAMPLE 2

The compound, 5-amino-2-(4-chlorobenzyloxy)pyridine is prepared from 2-chloro-5-nitropyridine and 4-chlorobenzyl alcohol and then reacted with 3,4,5,6-tetrahydrophthalic anhydride using the procedure of Example 1 to yield N-[2-(4-chlorobenzyloxy)-5-pyridyl]-3,4,5,6-tetrahydrophthalimide.

NMR (CDCl$_3$) 1.80 (br m, 4, ring CH$_2$) 2.4 (br m, 4, allylic ring CH$_2$) 5.32 (S, 2, φ CH$_2$) 6.73–8.1 (m, 3, pyridyl H) and 7.30 ppm (S, 4, φ H).

EXAMPLE 3

(A) The compound, 2-amino-5-(4-chlorobenzyloxy)pyridine is reacted with 3,4,5,6-tetrahydrophthalic anhydride using the procedure of Example 1 to yield N-[5-(4-chlorobenzyloxy)-2-pyridyl]-3,4,5,6-tetrahydrophthalimide.

(B) A mixture of 5-hydroxy-2-nitropyridine (7 g), K$_2$CO$_3$ (6.9 g) of DMF (100 ml) is stirred for about 10 minutes. To the mixture is added 4-chlorobenzyl chloride (8.1 g) in portions over about 15 minutes. The reaction mixture is stirred about 16 hours and then heated to 45° for about 30 minutes. After cooling, the reaction is diluted with CHCl$_3$, washed with water and saturated NaCl, dried (Na$_2$SO$_4$) and stripped. The crystalline solid is washed with 20% ethyl acetate/hexane, giving 5-(4-chlorobenzyloxy)-2-nitropyridine.

A mixture of 5-(4-chlorobenzyloxy)-2-nitropyridine (0.5 g), Na$_2$S (0.25 g) and methanol (12 ml) is heated to reflux for about 3 hours. Then, a few drops of water is added and refluxing continued about 15 hours. After cooling, the reaction is diluted with methanol, filtered through celite and stripped. The concentrate is taken up in CHCl$_3$, washed with water, dried and stripped giving 2-amino-5-(4-chlorobenzyloxy)pyridine.

EXAMPLE 4

Each of the substituted amino pyridines under Col. I is reacted with 3,4,5,6-tetrahydrophthalic anhydride using the procedure of Example 1 to prepare the compound of formula (A) under Col. II. The substituted amino pyridines under Col. I are prepared by the procedure of Example 3 (B).

I 2-amino-5-benzyloxypyridine
2-amino-5-(4-bromobenzyloxy)pyridine
2-amino-5-(4-chloro-3-methylbenzyloxy)pyridine
2-amino-4-chloro-5-benzyloxypyridine
2-amino-4-chloro-5-(4-chlorobenzyloxy)pyridine

II

N-(5-benzyloxy-2-pyridyl)-3,4,5,6-tetrahydrophthalimide
N-[5-(4-bromobenzyloxy)-2-pyridyl]-3,4,5,6-tetrahydrophthalimide
N-[5-(4-chloro-3-methylbenzyloxy)-2-pyridyl]-3,4,5,6-tetrahydrophthalimide
N-(5-benzyloxy-4-chloro-2-pyridyl)-3,4,5,6-tetrahydrophthalimide
N-[5-(4-chlorobenzyloxy)-4-chloro-2-pyridyl]-3,4,5,6-tetrahydrophthalimide.

EXAMPLE 5

A mixture of 2-amino-6-hydroxypyridine (2.2 g), 3,4,5,6-tetrahydrophthalic anhydride (3.0 g) and acetic acid (40 ml) is heated to reflux for about 18 hours. The reaction is then cooled and stripped. The concentrate is taken up in CHCl$_3$ (100 ml), washed with water, dried and stripped to yield N-(6-hydroxy-2-pyridyl)-3,4,5,6-tetrahydrophthalimide.

A mixture of N-(6-hydroxy-2-pyridyl)-3,4,5,6-tetrahydrophthalimide (3.9 g), silver carbonate (2.2 g), p-chlorobenzyl chloride (2.6 g) and benzene (75 ml) is stirred, in the dark, at 45° for about 72 hours. Then, the reaction is cooled and filtered. The filtrate is washed with 10% sodium bicarbonate and water, dried and stripped to give N-[6-(4-chlorobenzyloxy)-2-pyridyl]-3,4,5,6-tetrahydrophthalimide.

Benzyl chloride is used in place of p-chlorobenzyl chloride in the above procedure to give N-(6-benzyloxy-2-pyridyl)-3,4,5,6-tetrahydrophthalimide.

In Example 3, the use of 4-trifluoromethylbenzyl chloride in place of 4-chlorobenzyl chloride gives 2-nitro-5-(4-trifluoromethylbenzyloxy)pyridine which is reduced to the corresponding 2-amino-substituted pyridine which is reacted with 3,4,5,6-tetrahydrophthalic anhydride to yield N-[5-(4-trifluoromethylbenzyloxy)-2-pyridyl]-3,4,5,6-tetrahyrophthalimide.

Post-emergence herbicide activity of the compound of Example 2 (N-[4-chlorobenzyloxy)-5-pyridyl]-3,4,5,6-tetrahydrophthalimide) was tested on the grasses (GR) greenfoxtail, watergrass, shattercane and wildoats and on the broadleafs (BL) annual morningglory, mustard, soybean and velvetleaf by spraying at a rate equivalent to 10 lb/acre with the result of average percent injury of 65 and 95, respectively.

Pre-emergence herbicide activity of the compound of Example 2 on the same grasses and the broadleafs annula morningglory, mustard, nightshade and velvetleaf at the rate of 10 lb/acre gave average percent injury of 89 and 83, respectively.

EXAMPLE 6

To prewashed NaH (3×20 ml hexane) (2.52 g active NaH, 105 mmol) in dimethylformamide (DMF) (50 ml) is added 3-hydroxypyridine (10.0 g, 105 mmol) in DMF (50 ml) with cooling over 0.5 hour. The reaction mixture is stirred at RT for 1 hour and is then cooled to 15°. To this is rapidly added 4-chlorobenzyl chloride (16.25 g, 99.8 mmol) in 5 ml of DMF. The reaction is allowed to warm to RT, and is then poured into ice and extracted with chloroform (3×). The chloroform layers are combined, washed with water and with brine, dried over calcium sulfate and rotoevaporated. The crude product is poured into ice and extracted with ether (3×). The combined ether layers are washed with water and with brine, and dried over calcium sulfate to give 3-(4-chlorobenzyloxy)pyridine.

To 3-(4-chlorobenzyloxy)pyridine (2.19 g, 10 mmol) in formamide (10 ml) at 10° is slowly added conc. sulfuric acid. The reaction is then cooled to 5°, and $FeSO_4.7H_2O$ (4.16 g, 15 mmol), finely powdered, and hydrogen peroxide (1.7 ml of 30% solution, 0.51 g of $H_2O_2$, 15 mmol) are added simultaneously over 10 minutes, with rapid stirring and cooling to 12°–18°. After addition is complete, the reaction is allowed to sit at RT overnight. Ethyl acetate and water are added to the reaction slurry. The layers are separated, and the aqueous phase is extracted with ethyl acetate (3×). The combined organic layers are washed with water and with brine and are dried over calcium sulfate. The residue is taken up in ether, leaving an oily residue. The oily residue is then taken up in chloroform, washed with sat. sodium carbonate, with water and with brine and purified by preparative thin layer chromatography (developing with 50% ethyl acetate/hexane and 0.05% ammonium hydroxide). The second band is collected, yielding 5-(4-chlorobenzyloxy)pyridine-2-carboxamide.

To sodium methoxide (13.5 mg, 0.59 mmol, of sodium in methanol) in methanol at −5° is added 5-(4-chlorobenzyloxy)pyridine-2-carboxamide (73 mg, 0.28 mmol), followed by addition of bromine (44.5 mg, 0.28 mmol). After the white solid has dissolved ($\approx$5 min.), the reaction is allowed to warm to RT and then is heated rapidly to reflux. After 2 hours at reflux temperature, the reaction is allowed to cool to RT and rotoevaporated to remove the alcohol. The reaction is then poured into water, neutralized with 2 N sulfuric acid and extracted with excess ethyl acetate. The organic phase is washed with water and with brine, dried over calcium sulfate, filtered and rotoevaporated to yield methyl N-[5-(4-chlorobenxyloxy)-2-pyridyl]-carbamate.

10% Sodium hydroxide (8 ml) is added to methyl N-[5-(4-chlorobenzyloxy)-2-pyridyl]carbamate (59 mg, 0.20 mmol), and the mixture is heated rapidly to 85°. About 4 ml of methanol is added to the mixture after it has been heated for 2 hours. Heating is continued, and after another hour about 4 ml more of methanol is added to the mixture. Heating at 85° is continued overnight. The reaction is then cooled, and the methanol is rotoevaporated off. The reaction is poured into water and extracted with chloroform. The organic phase is washed with water and with brine to yield 2-amino-5-(4-chlorobenzyloxy)pyridine.

nmr ($CDCL_3$) δ 4.10 (b s, 2, $NH_2$), 4.85 (s, 2, —OCH$_2$Ar), 6.32 (d, 1, pyridylC-4H, 9 Hz), 7.01 cm, 1, pyridylC-3-H, 9 Hz and 2.5 Hz), 7.23 (s, 4, phenyl protons) and 7.68 ppm (m, 1, pyridylC-6H, 2.5 Hz).

EXAMPLE 7

Each of the substituted amino pyridines under Col. III may be prepared by the procedure of Example 6 from the respective corresponding substituted benzyl chloride and 3-hydroxypyridine.

III 2-amino-5-benzyloxypyridine
2-amino-5-(4-bromobenzyloxy)pyridine
2-amino-5-(4-chloro-3-methylbenzyloxy)pyridine
2-amino-5-(-4-trifluoromethylbenzyloxy)pyridine Likewise, 2-amino-4-chloro-5-benzyloxypyridine and 2-amino-4-chloro-5-(4-chlorobenzyloxy)pyridine may be prepared from 3-hydroxy-4-chloropyridine and, respectively, benzyl chloride and 4-chlorobenzyl chloride.

EXAMPLE 8

Following the procedure of Example 6, 2-amino-5-(4-chlorophenethoxy)pyridine and 2-amino-5-(4-methylphenethoxy)pyridine are prepared from 3-hydroxypyridine and, respectively, 4-chlorophenethyl chloride and 4-methyl phenethyl chloride.

EXAMPLE 9

To sodium hydroxide (50% oil dispersion, 43.2 g, 21.6 g of active NaH, 900 mmol), prewashed in dry hexane, in 800 ml of dimethylformamide (DMF) is added 5-hydroxy-2-methylpyridine (98.8 g, 906 mmol) in 700 ml of DMF at 15° and over 0.75 hour. The reaction is allowed to warm to RT and is stirred for 2 hours. It is then cooled to 10°, and methyliodide is added over 0.5 hour. The reaction is again allowed to warm to RT and is stirred overnight. It is then filtered through celite, and the solid is washed with chloroform, filtered and rotoevaporated. The resulting solid is washed with chloroform 3×, and is stirred with chloroform overnight. It is filtered and rotoevaporated, after which ether is added, followed by 10% sodium hydroxide and water. The mixture is extracted with ether (3×). The combined ether extracts are washed with water and with brine, dried over calcium sulfate, filtered and rotoevaporated to give 5-methoxy-2-methylpyridine.

To 5-methoxy-2-methylpyridine (26 g, 212 mmol) in water at 90° is added potassium permanganate (150 g, 955 mmol) in portions over 4 hours. The reaction is stirred at 85° for 0.5 hours, and is then allowed to cool to RT. It is filtered through celite, and the solid is washed with 60° water (3×) and is rotoevaporated. Water is added, with stirring, to the residue just until all solid is dissolved (200 ml $H_2O$). The pH is adjusted to 4±.2 with conc. hydrochloric acid. A white solid precipitates and is filtered out. The aqueous layer is extracted wiith ethyl acetate (3×) and the pH is again adjusted to 4. Continuous extraction with ethyl acetate proceeds for 4 days. The desired material is isolated from the ethyl acetate extracts. Toluene is added (∼150 ml) and the mixture is filtered. Toluene is again added and the mixture is azeotroped to give 5-methoxy-2-pyridylcarboxylic acid.

To 5-methoxy-2-pyridylcarboxylic acid (11.9 g, 77.5 mmol) and DMF (5.4 ml, 69 mmol) in 200 ml of tetrahydrofuran (THF) at 5° is added thionyl chloride (8.4 ml, 116 mmol) over 15 minutes. After addition, the slurry is allowed to warm slowly to RT. After 3 hours, the reaction is rotoevaporated to give 5-methoxy-2-pyridylcarboxylic acid chloride. This acid chloride is gradually added, with cooling, to rapidly stirring ammonium hydroxide (40 ml, 340 mmol), and the slurry is stirred for 1 hour. The reaction is filtered and the residue is dried. To this is added dry toluene, with stirring, followed by filtration. More toluene is added, followed by rotoevaporation to give 5-methoxy-2-pyridylcarboxamide.

To 5-methoxy-2-pyridylcarboxamide (2 g, 13.2 mmol) in 5 ml of DMF at RT is added the sodium salt of ethanethiol (26.3 mmol) in DMF (61.5 ml). The slurry is heated to 110° with stirring for about 15 minutes. The reaction is cooled to 50° and 40 ml of DMF is added. After 0.5 hour, the reaction is cooled to 10° and 4-chlorobenzyl chloride (2.47 g, 15.4 mmol) is added. The reaction is allowed to warm to RT and is stirred for 3 days. About 0.5 ml of 4-chlorobenzyl chloride/DMF (0.21 g/1 ml) is added. After 2 hours at RT, the reaction is poured into ice water and ethyl acetate. The ethyl acetate is extracted off, and the water layer is extracted with ethyl acetate (4×). The combined organic layers are washed with water and with brine, dried, filtered and rotoevaporated. The residue is washed with 20% ether/hexane (4×). The liquid is pipetted off and the residue is rotoevaporated to give 5-(4-chlorobenzyloxy)-2-pyridylcarboxamide.

Sodium (0.8 g, 34.8 mmol) is combined with methanol (80 ml) and is cooled to −10°. To this solution at −10° is added 5-(4-chlorobenzyloxy)-2-pyridylcarboxamide (1.98 g, 7.5 mmol). Bromine is slowly added over 15 minutes with stirring, keeping the temperature at −5°. The reaction is stirred at −5°–0° for 10 minutes and is then allowed to warm to RT. The reaction is heated under reflux for 1.5 hours and is then allowed to return to RT. The methanol is rotoevaporated off, and ethyl acetate (200 ml) and ice water (200 ml) are added to the residue, followed by several drop of 2 N sulfuric acid to neutralize. The mixture is extracted with ethyl acetate (4×), and the combined organic layers are washed with brine and rotoevaporated. Toluene is added, and the residue is rotoevaporated and purified by prep. TLC. The least polar band is collected to give methyl 5-(4-chlorobenzyloxy)-2-pyridylcarbamate.

A slurry of methyl 5-(4-chlorobenzyloxy)-2-pyridylcarbamate (0.75 g, 2.6 mmol) in 10% sodium hydroxide (20 ml) and methanol (40 ml) is heated to 90° under nitrogen gas. After 1 hour, 10 ml of 10% sodium hydroxide and 10 ml of methanol are added. Heating is continued, and after 2 hours, 10 ml of methanol is added. The reaction is heated under reflux overnight. The reaction is then rotoevaporated, and chloroform and water are added. The residue is extracted with chloroform (4×). The combined chloroform extracts are washed with water until neutral and with brine, dried over calcium sulfate, filtered and rotoevaporated to yield 2-amino-5-(4-chlorobenzyloxy)pyridine.

What is claimed is:

1. A compound selected from those of the following formula (A):

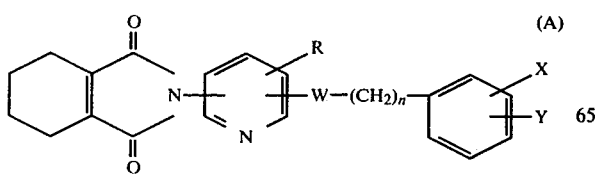

(A)

wherein,
n is one, two or three;
R is hydrogen, bromo, chloro, fluoro or iodo;
W is oxygen or sulfur; and
each of X and Y is, independently, selected from hydrogen, bromo, chloro, fluoro, iodo, lower alkyl, lower alkoxy, lower thioalkyl, lower haloalkyl, lower haloalkoxy.

2. A compound according to claim 1 of the formula:

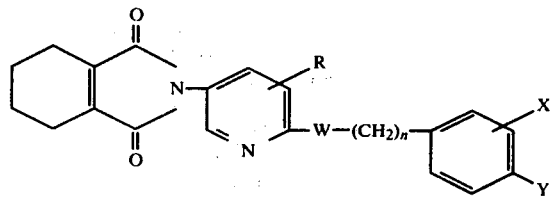

3. A compound according to claim 1 of the formula:

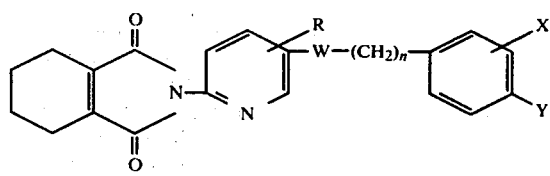

4. A compound according to claim 1 of the formula:

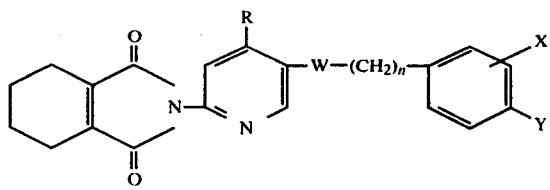

5. A compound according to claim 1 of the formula:

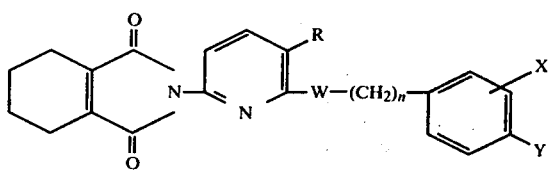

6. A compound according to claim 1 of the formula:

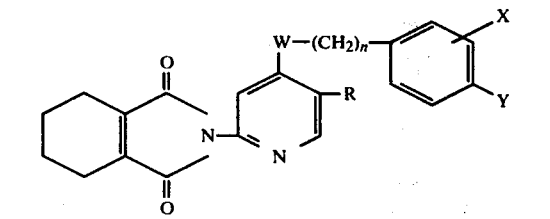

7. A compound according to claim 1 wherein R is hydrogen or chloro, W is oxygen, n is one and each of X and Y is independently selected from hydrogen and chloro.

8. A compound according to claim 7 wherein R is hydrogen, X is hydrogen and Y is chloro.

9. A compound according to claim 2 wherein R is hydrogen or chloro, W is oxygen, n is one and each of X and Y is independently selected from hydrogen and chloro.

10. A compound according to claim 9 wherein R is hydrogen, X is hydrogen and Y is chloro.

11. A compound according to claim 3 wherein R is hydrogen or chloro, n is one and X is hydrogen, chloro or methyl.

12. A compound according to claim 11 wherein W is oxygen and Y is hydrogen, bromo or chloro.

13. A compound according to claim 12 wherein R is hydrogen, X is hydrogen and Y is chloro.

14. A compound according to claim 11 wherein W is oxygen and each of R, X and Y is hydrogen.

15. A compound according to claim 12 wherein each of R and X is hydrogen and Y is bromo.

16. A compound according to claim 4 wherein R is chloro, W is oxygen, n is one, X is hydrogen, chloro or methyl, and Y is hydrogen, bromo or chloro.

17. A compound according to claim 16 wherein X is hydrogen and Y is bromo or chloro.

18. A compound according to claim 5 wherein R is chloro, W is oxygen, n is one, X is hydrogen, chloro or methyl, and Y is hydrogen, bromo or chloro.

19. A compound according to claim 18 wherein X is hydrogen and Y is bromo or chloro.

20. A compound according to claim 6 wherein R is hydrogen or chloro, W is oxygen, n is one, X is hydrogen, chloro or methyl and Y is hydrogen, bromo or chloro.

21. A compound according to claim 20 wherein R is hydrogen.

22. A compound according to claim 21 wherein X is hydrogen and Y is bromo or chloro.

23. A compound according to claim 20 wherein R is chloro and X is hydrogen.

24. A compound according to claim 23 wherein Y is bromo or chloro.

25. A method for the control of plants which comprises treating said plant with an effective amount of a compound of formula (A) as defined in claim 1.

26. The method according to claim 25 wherein the plant is a weed and said effective amount is a herbicidally effective amount.

27. The method according to claim 26 wherein the soil is treated prior to germination of the seed of said plant.

* * * * *